United States Patent [19]

Schneider

[11] Patent Number: 5,346,479
[45] Date of Patent: Sep. 13, 1994

[54] RETENTION DEVICE

[75] Inventor: Barry L. Schneider, McHenry, Ill.

[73] Assignee: Hollister Incorporated, Libertyville, Ill.

[21] Appl. No.: 79,016

[22] Filed: Jun. 18, 1993

Related U.S. Application Data

[63] Continuation-in-part of Ser. No. 895,335, Jun. 8, 1992, Pat. No. 5,267,967.

[51] Int. Cl.$^5$ ............... A61M 5/32; B65D 63/00; B65D 67/02
[52] U.S. Cl. ............... 604/174; 128/DIG. 6; 604/177; 604/178; 604/179; 604/180; 24/16 PB
[58] Field of Search ............... 128/DIG. 6; 604/174, 604/177–180; 24/16 PB, 17 AP, 30.5 P, 306; 248/74.2, 74.3

[56] References Cited

U.S. PATENT DOCUMENTS 5,267,967 12/1993 Schneider .................. 604/174

Primary Examiner—Randall L. Green
Assistant Examiner—P. Zuttarelli
Attorney, Agent, or Firm—Tilton, Fallon, Lungmus & Chestnut

[57] ABSTRACT

A retention device, particularly useful for drainage tubes and the like, having a pad for adhesive attachment to a patient's skin at the exit/entry site for a post-surgical drainage tube. The device includes a retainer body secured to the pad and provided with a strap to be looped and tightened about the drainage tube for immobilizing that tube. A passage in the body receives the free end of the strap and a latching mechanism prevents retraction of the strap unless the sides of the body are squeezed towards each other to alter the configuration of the body's side and top walls and cause lateral disengagement of a restraining pawl from the ratchet teeth of the strap.

13 Claims, 4 Drawing Sheets

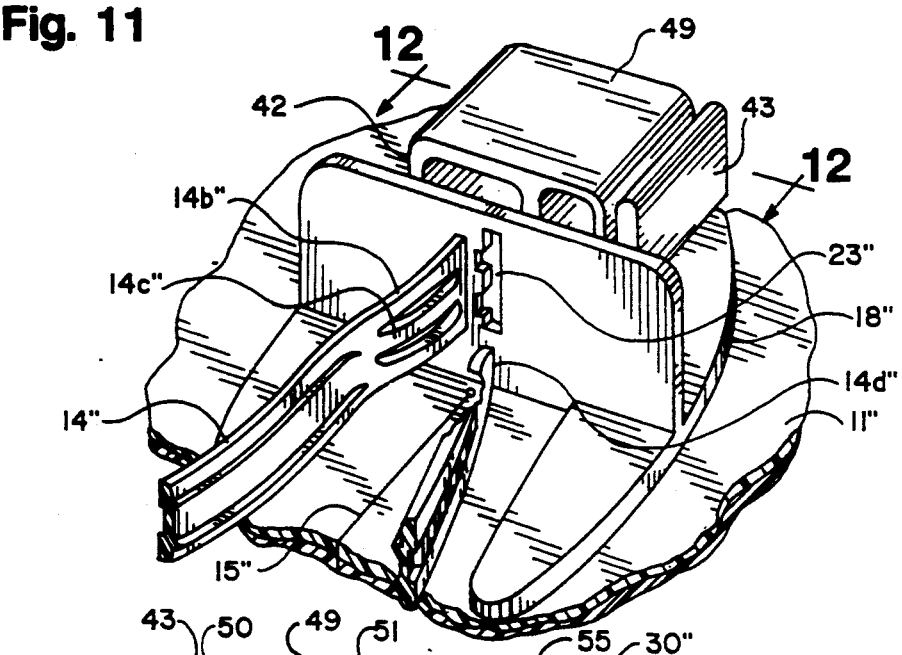
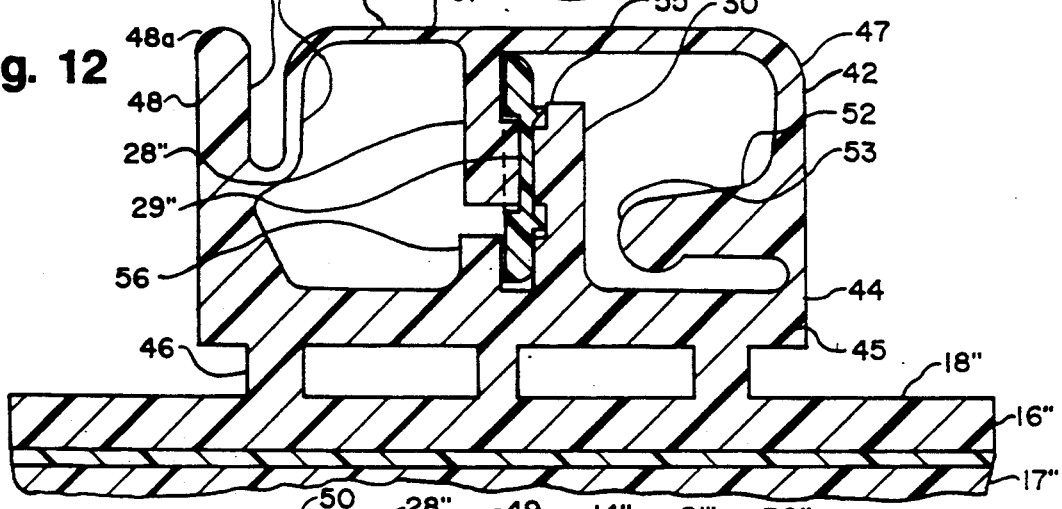
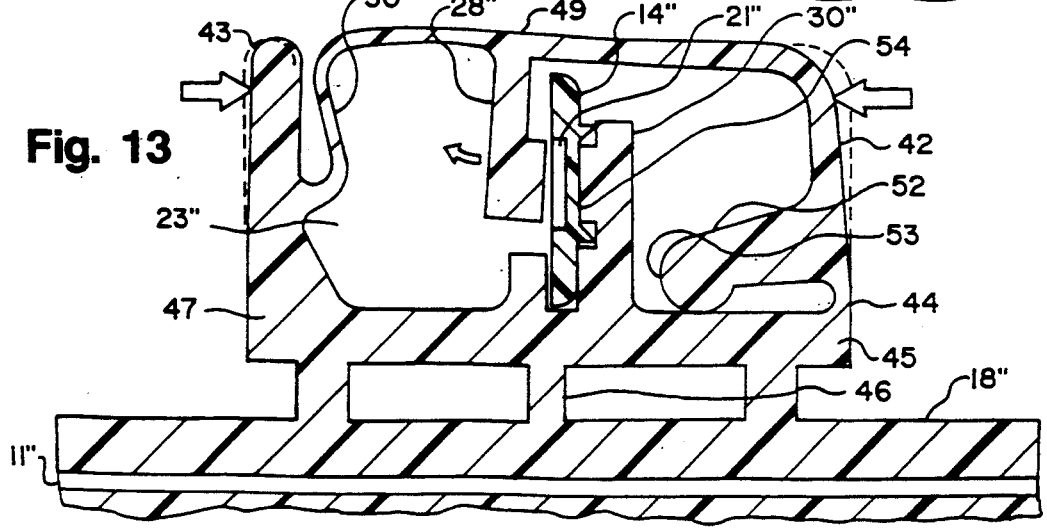

RETENTION DEVICE

This application is a continuation-in-part of application Ser. No. 07/895,335, filed Jun. 8, 1992 now U.S. Pat. No. 5,267,967.

BACKGROUND AND SUMMARY

Co-owned U.S. Pat. No. 5,073,170 discloses a retention device having an adhesive pad and a tube retainer secured to the pad's upper surface. A flexible strap extends from one side of the retainer and may be looped about a drainage tube so that when the strap's free end is inserted through a passage in the retainer body containing a detent or latch mechanism, the strap may be drawn tightly about the tube to immobilize the same. The Y-shaped configuration of the strap with its diverging arms secured to the retainer on opposite sides of the entrance opening to the passage permits the strap to be drawn tightly about even the smallest drainage tubes or catheters in common use.

While the patented device is highly effective in securing immobilizing drainage tubes over a wide range of sizes, the procedure for releasing the latching mechanism may not be immediately apparent to an attendant unfamiliar with the device. Such release involves lifting an exposed extension or handle of the latching member located within the passage. The lifting action may be awkward to perform and, even if done properly, may result in the transmission of pulling forces to the skin areas surrounding the exit site. Pulling or lifting forces applied to that site may cause considerable patient discomfort. To reduce such discomfort, the attendant may use the fingers of his/her other hand to restrain movement of the adhesive pad as the latching member is raised. While such a measure may avoid or reduce discomfort, it requires the use of both hands, leaving no hand free for the attendant to retract the strap from the passage when the latching member has been so raised.

In addition, it has now been found that while the patented device operates with a wide range of tube sizes and is especially effective in retaining drainage tubes of the smaller sizes (which prior retention devices often failed in securely restraining), the forces required to draw the strap tightly about larger-sized tubes tends to be greater than for smaller tubes because of the sharper directional change of the strap as it enters the retainer body. Again, the need for applying added force not only presents operational problems but would be expected to add to patient discomfort.

Accordingly, it is a main aspect of this invention to provide an improved tube retention device which is easily operated with tubes over the full range of sizes and which minimizes if not eliminates patient discomfort when the device is operated to secure or release a drainage tube. Problems of patient discomfort caused by the transmission of pushing or pulling forces towards or away from the skin surface are eliminated, or at least greatly reduced, because the forces required to operate the device are balanced and are not exerted in directions perpendicular to that surface. To release the latch mechanism, a user simply squeezes the sides of the tube retainer with such opposing and offsetting forces being applied in directions parallel with the patient's skin.

Briefly, the device takes the form of a flexible pad having upper and lower surfaces and with a pressure-sensitive adhesive layer along its lower surface for adherence to a patient's skin. A tube retainer is mounted upon the pad's upper surface and includes a retainer body having a passage extending therethrough. An elongated strap has one end portion joined to the body adjacent the entrance to the passage and an opposite free end portion insertable into and through the passage. When so inserted, the strap forms a loop for receiving and holding a drainage tube.

In a preferred embodiment, the retainer body includes a platform and first and second vertical side walls extending along the passage, the first side wall being substantially flexible and pivotally connected to the platform whereas the second side wall is substantially rigid. A flexible top wall is joined to an upper portion of the first side wall at one end and a flexible web joins the other end to an intermediate portion of the second side wall. The web and the second side wall are spaced apart so that when the first side wall is squeezed towards the second side wall, the web will deform towards the second side wall and allow the first side wall and top wall to laterally cant toward the second side wall. A pawl or latch member extends downwardly from a central portion of the top wall for engaging the ratchet teeth of the strap and preventing reverse movement of the strap in the passage unless and until the first side wall is squeezed toward the second side wall between the operator's fingers.

The device may have its strap oriented so that the axis of the loop (or the plane of the strap) extends either horizontally or vertically. In an embodiment in which the orientation is vertical, the strap is joined to the retainer body close to the entrance to the strap-receiving passage so that the vertical surface of a guide member or wall within that passage lies along a plane that substantially bisects the loop formed by the strap when the strap is tightened about a drainage tube. Approximately equal portions of the loop are thereby disposed on each side of that plane to reduce the sharpness of the curvature of the strap that would otherwise develop at the entrance to the passage if such portions were unequal in size.

Other features, advantages, and objects of the invention will become apparent from the specification and drawings.

DRAWING

FIG. 11 is a fragmentary perspective view depicting an embodiment of the invention in which the plane of the strap extends vertically.

FIG. 12 is a cross sectional view illustrating the embodiment of FIG. 11 with the strap inserted and latched.

FIG. 13 is a sectional view similar to FIG. 12 but showing the first flexible wall squeezed toward the second rigid wall for releasing the latch mechanism.

DETAILED DESCRIPTION OF PREFERRED EMBODIMENTS

Figure 1:
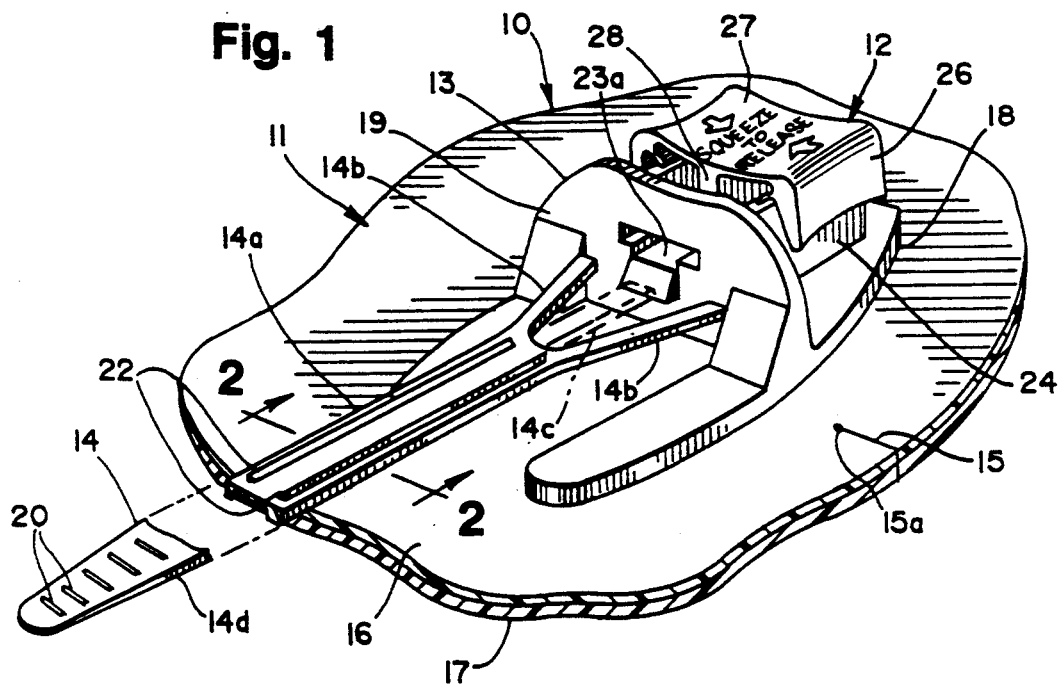
FIG. 1 is a fragmentary perspective view of a drainage tube attachment device embodying the invention.
Figure 2:
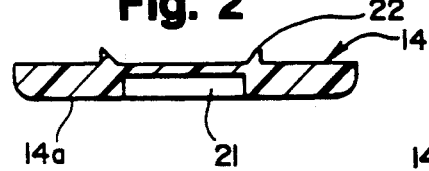
FIG. 2 is an enlarged sectional view of the strap taken along line 2—2 of FIG. 1.

Referring to FIGS. 1-7 of the drawings, numeral 10 generally designates a drainage tube retention device composed of a flexible adhesive pad 11 and retaining means 12 in the form of a retainer body 13 and an integral strap 14. The illustrated pad is planar and may have a periphery (not shown) of various shapes although circular is believed preferable. A radial entry slit 15 extends transversely with respect to the tube retainer, terminating in close proximity to that retainer. Preferably, the slit terminates with its inner end 15a near the center of the pad with the retainer 12 being offset from the pad's center point. Such a relationship, as disclosed in aforementioned U.S. Pat. No. 5,073,170, allows the pad to be centered over an exit opening for a drainage tube or catheter with the tube then extending generally upwardly through the center of the pad.

The materials and construction of the pad may be as disclosed in the aforementioned patent. In one such construction, pad 11 is composed of an upper layer 16 of resilient, flexible, fine-celled thermoplastic foam, such as polyolefin or polyurethane foam, and a lower layer 17 of soft, deformable skin barrier material having both wet and dry tack. If desired, the upper layer 16 may be formed of materials other than foam, such as a film of flexible polyurethane or other polymeric film having similar properties, and lower layer 17 may instead be formed of a suitable pressure-sensitive adhesive (e.g., a medical-grade acrylic adhesive).

The tube retainer 12 is a unitary part molded from polypropylene, nylon, or other flexible thermoplastic material and includes a generally planar plate 18 which is secured by adhesive or any other suitable means to the upper surface of pad 11. The retainer body 13 extends upwardly from the plate and includes a transverse front wall 19 to which one end of strap 14 is integrally joined. As in U.S. Pat. No. 5,073,170, strap 14 is Y-shaped in configuration and includes an elongated central tongue portion 14a and a pair of diverging limb portions 14b. The strap may also include a central limb portion 14c between the diverging portions 14b of the Y-shaped strap, although such central portion may be omitted if desired. The tongue portion of the strap is of substantially uniform width throughout its full length and the free end 14d is rounded and tapered. Free end 14d may also have a series of transverse ridges 20 to facilitate gripping the end of the strap between the fingers when the device is being readied for immobilizing a drainage tube. The underside of the tongue is provided with a longitudinal series of transversely extending ratchet teeth 21 and the upper surface may be provided with a pair of parallel, longitudinally-extending ribs 22.

Figure 3:
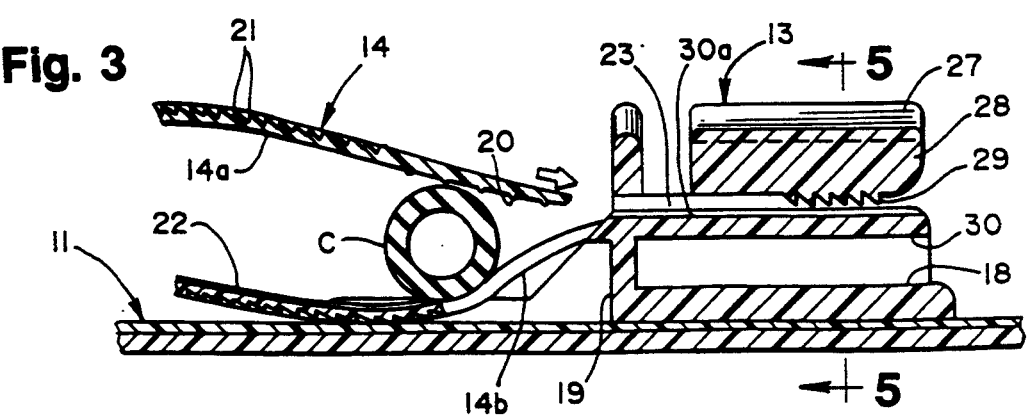
FIG. 3 is a fragmentary longitudinal sectional view showing the free end of the strap positioned for insertion into the passage of the retainer body.
Figure 5:
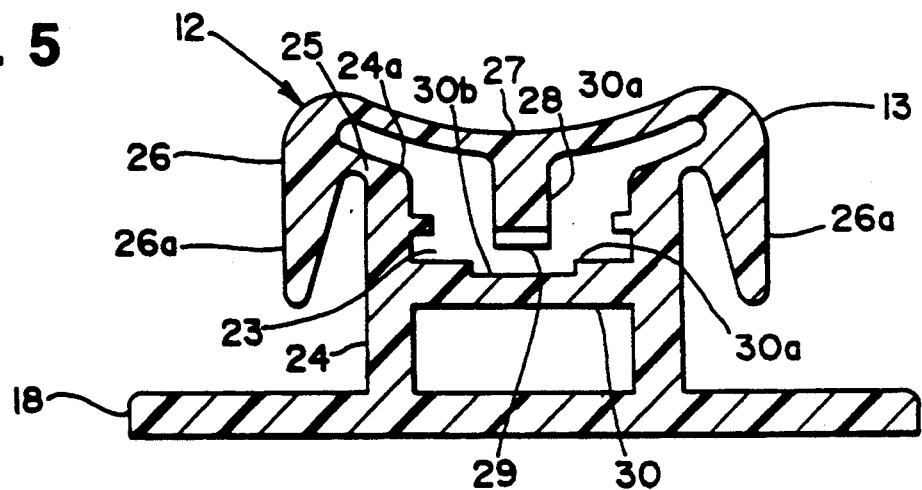
FIG. 5 is a still further enlarged cross sectional view taken along line 5—5 of FIG. 3.

The retainer body 13 has a horizontal passage 23 aligned with strap 14, the entrance 23a to the passage being located in the transverse front wall 19 between and slightly above the diverging arms or limbs 14b of the strap (FIGS. 1, 3). Referring to FIG. 5, the body 13 includes a pair of upstanding side walls 24 extending along passage 23 and pivotally connected at their upper ends by thin, flexible web portions 25 to a pair of lever arms or flanges 26. The lever arms 26 have relatively thick, rigid lower portions 26a extending downwardly below the webs (and below the upper edges 24a of the side walls) and upper portions 26b projecting above web portions 25. A flexible top wall 27 joins the upper portions of the two lever arms and, as shown clearly in FIG. 5, the top wall normally curves downwardly toward passage 23 when the body is in a relaxed or untensioned state (FIG. 5). In that state, the lever arms 26, and particularly the lower portions 26a of those arms, are spaced substantially from the outer surfaces of side walls 24.

Figure 4:
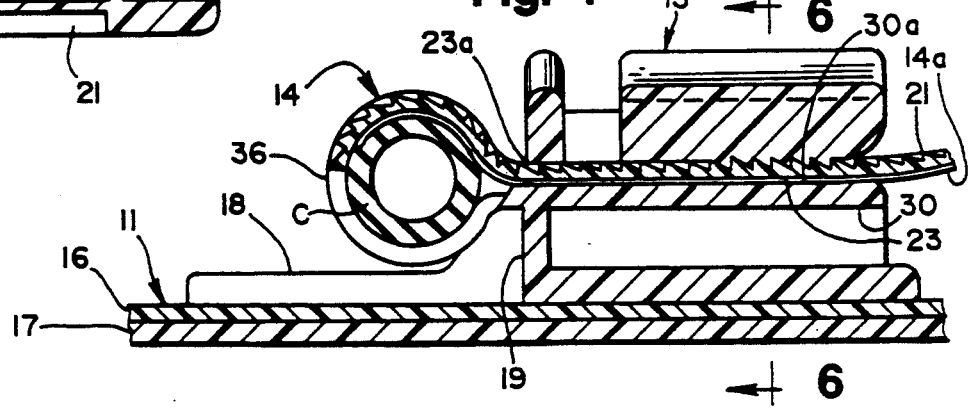
FIG. 4 is a sectional view similar to (but on a scale slightly larger than) FIG. 3, showing the strap in latched condition drawn tightly about a drainage tube.
Figure 6:
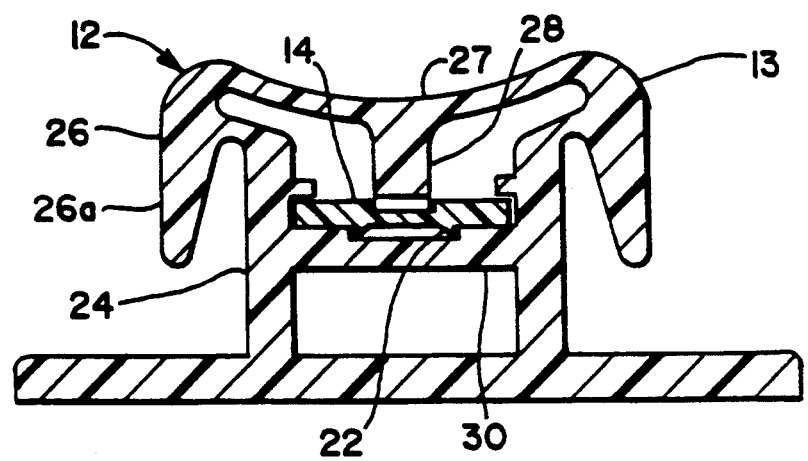
FIG. 6 is a cross sectional view similar to FIG. 5 but taken along line 6—6 of FIG. 4.
Figure 7:
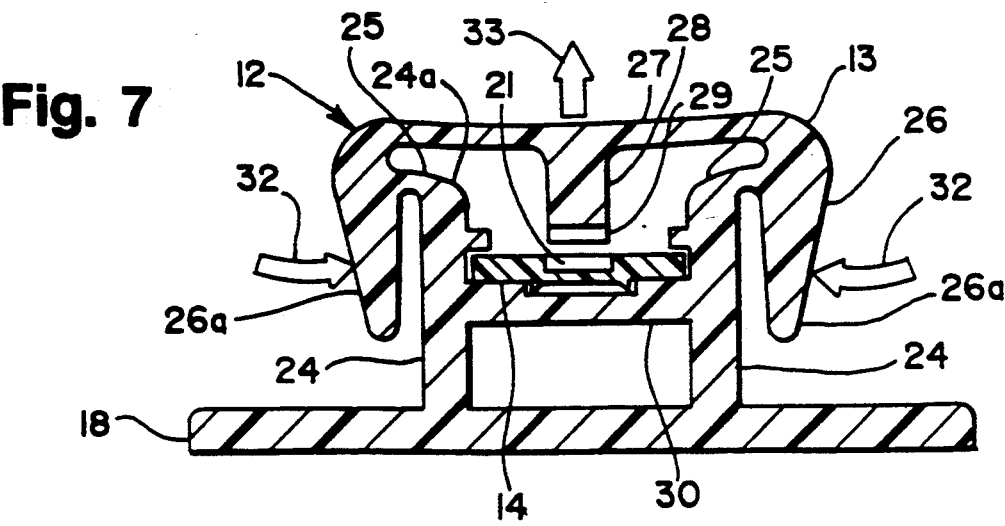
FIG. 7 is a cross sectional view similar to FIGS. 5 and 6 but showing the changes occurring when the lever arms of the retainer body are squeezed towards each other.

Detent means in the form of a latching member 27 is formed integrally with top wall 28 and projects downwardly from the central portion of that top wall. The latching member is provided with one or more teeth 29 (FIG. 3) and functions as a pawl for engaging the ratchet teeth of strap 14 when the strap is inserted into the passage as depicted in FIGS. 4 and 6.

Body 13 also includes a guide wall 30 which is parallel with plate 18 and pad 11 and has a top surface 30a spaced well above the upper surface of the pad. The guide wall is imperforate and includes an upwardly-facing channel 30b that extends the length of passage 23 and receives the longitudinal ribs 22 of the strap (FIG. 6).

The parts are dimensioned so that when the free end of the strap is inserted into passage 23 the ratchet teeth of the strap will engage the teeth of the pawl or latch member 28, causing top wall 27 to flex slightly upwardly as the teeth of the respective parts clear each other and then return a limited distance downwardly to maintain the teeth of the respective parts in forceful interlocking engagement. Retraction of the strap is prevented by the intermeshing teeth unless the top wall 27 and latch member 28 are lifted to shift the teeth of the pawl out of engagement with those of the strap.

Release of the latch mechanism occurs when the lever arms 26 along each side of the body 13 are squeezed towards each other in the directions of arrows 32 (FIG. 7), causing the arms to pivot about the webs 25 at the upper edges 24a of side walls 24 and producing at least a partial straightening of top wall 27. As the curvature in the top wall is reduced, the central portion of that wall shifts upwardly in the direction of arrow 33, lifting the teeth 29 of the latching member or pawl 28 out of engagement with teeth 21 of strap 14. Since the lower portions of the lever arms may be easily pivoted towards each other by the fingers of one hand, the user's other hand remains available to retract the strap from passage 23. The squeezing of the lever arms is facilitated by the fact that the outer surfaces of those arms are elongated in the direction of the passage and have concave curvatures revealed most clearly in FIG. 1. Since the lever arms 26 extend downwardly in the same directions as the user's fingers, the pivoting action of the lever arms corresponds with the closing action of the thumb and an opposing index or middle finger engaging the respective concave surfaces of the two arms.

Of particular importance is the fact that the forces exerted upon the retainer 12 to release the latching mechanism are applied in two opposing directions extending in a plane parallel with that of plate 18 and pad 11. As a result, release of the strap may be accomplished without pulling the device away from the wound site or pushing it towards that site. While lateral forces are applied to the device, those forces neutralize or balanced off against each other and, therefore, are not transmitted to any appreciable extent to the patient.

As shown in FIG. 4, when the device is in operative position strap 14 forms a loop 36 about a drainage tube or catheter C. Since the top surface 30a of guide wall 30 is spaced well above the upper surface of pad 11, the loop is free to center itself so that surface 30a is in a plane that substantially bisects the loop 36 and tube C along axial directions. Approximately equal portions of the loop are disposed above and below the plane of guide surface 30a. The change in direction of the strap loop as it enters passage 23 is generally matched by the change in direction of the strap at its point of origin where it commences its loop about tube C. The result is that the sharpness of the directional change of the strap adjacent passage entrance 23a is considerably less than would occur if the surface 30a of guide wall 30 were coplanar with the upper surface of pad 11. The disclosed construction permits tighter engagement of the strap about the tube for any given amount of tightening force applied to the strap and is particularly helpful in retaining larger-size tubes which require more abrupt changes in direction of the strap in the immediate vicinity of passage entrance 23a.

Figure 8:
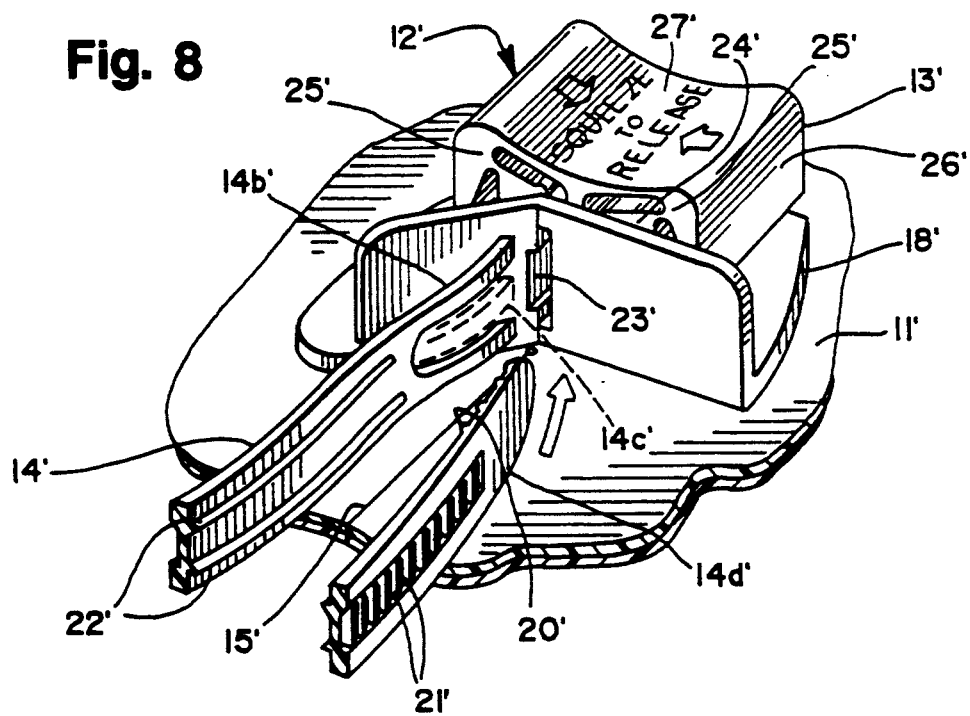
FIG. 8 is a fragmentary perspective view depicting a second embodiment of the invention in which the plane of the strap extends vertically.
Figure 9:
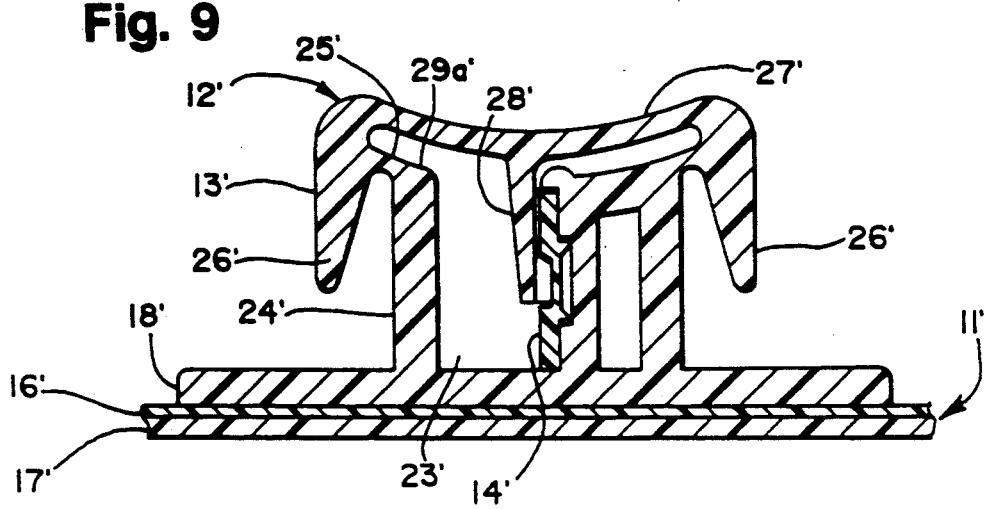
FIG. 9 is a cross sectional view illustrating the embodiment of FIG. 8 with the strap inserted and latched.
Figure 10:
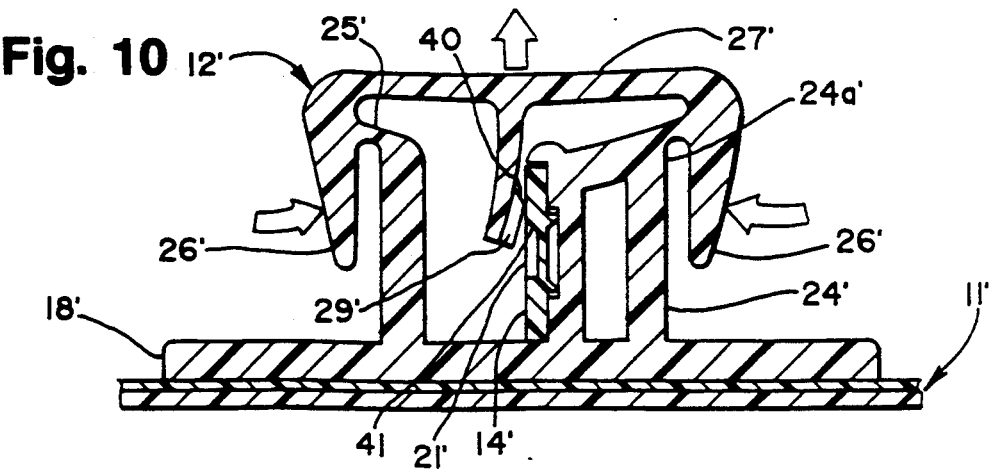
FIG. 10 is a sectional view similar to FIG. 9 but showing the lever arms squeezed towards each other for releasing the latch mechanism.

FIGS. 8-10 depict an embodiment which is similar to the one already described except that the strap 14' of the tube retaining means 12' is oriented vertically rather than horizontally. The loop that is formed by the strap therefore has its axis extending vertically and wraps about the portion of a tube or catheter that exits the patient's body in a direction substantially perpendicular to the skin surface. Like retainer 12, retainer 12' includes a body 13' having side walls 24' that extend upwardly from a plate or base 18' secured to the upper surface of a pad 11'. Thin, flexible webs 25' connect the upper edge portions 24a' of the side walls 24' to relatively rigid lever arms or flanges 26'. When the lever arms are squeezed towards each other, they pivot about the connecting webs 25' to cause the flexible top wall 27' to straighten, at least partially, and its central portion to shift upwardly along with the latching member or pawl 28' that extends downwardly into passage 23'. Teeth 29' of the pawl face laterally to engage the teeth 21' of the strap when the parts are latched together. It will be observed from FIGS. 9 and 10 that the upper ends of latching teeth 29' slope to define camming surfaces 40 and the strap 14' may also have a mating sloping surface or shoulder 41. As a result, when lever arms 26' are pivoted inwardly to raise the latching member, the slope of surfaces 40 and/or 41 cams the flexible latching member laterally to release the strap for withdrawal from the passage.

In both of the embodiments of FIGS. 1-7 and 8-10, the squeezing forces for releasing the latch mechanisms are applied in opposing directions extending generally in planes parallel with plates 18 and 18'. While it is preferred that such squeezing forces cause the lever arms 26, 26' on both sides of the retainer bodies to pivot inwardly, thereby raising the central portions of top walls 27, 27', it should be understood that a similar lifting action might result if only one of the lever arms of each pair were capable of pivoting inwardly with the other arm of the same pair being stationary and simply serving as a brace against which the squeezing force would be applied. For example, referring to FIG. 9, if the tapered space between the left lever arm 26' and side wall 24' were instead occupied by the plastic material from which the remainder of the retainer is formed, the left arm would be non-pivotal but would nevertheless serve as a brace when squeezing forces are applied to both of the arms 26'. In such a case, the lifting action on pawl 28' would result solely from the inward pivotal movement of right arm 26' and the resulting changes in configuration of top wall 27'. Therefore, while it is preferred that both of the lever arms of the two embodiments be capable of pivotal movement, many of the advantages of the invention may be accomplished if only one of the arms is pivotally mounted. In either case, the squeezing force for releasing the latch mechanism will be applied in a direction parallel with plate member 18, 18'.

FIGS. 11-13 depict another embodiment which is similar to the embodiments already described except that the squeezing forces for releasing the latch mechanism are applied to a first, substantially flexible side wall 42 and a second, substantially rigid side wall 43. First side wall 42 extends along passage 23", is pivotally connected by a web 44 to a platform 45 (positioned in parallel relation to and above plate 18" by a plurality of supports 46), and includes an upper portion 47. Second side wall 43 extends along passage 23", is rigidly fixed to platform 45, and includes an intermediate portion 48 and an upper edge portion 48a. A top wall 49 is joined to, or integrally formed with, upper portion 47 of first side wall 42 and is connected to a flexible web 50 which joins top wall 49 and intermediate portion 48 of second side wall 43. In its unflexed state, web 50 is spaced apart from and in parallel relation to second side wall 43 to allow top wall 49 and first side wall 42 to cant toward second side wall 43 when the two side walls are squeezed towards each other (as indicated by arrows in FIG. 13) and the first side wall 42 is thereby urged towards second side wall 43.

Top wall 49 has a central portion 51 which has a downwardly extending latching member or pawl 28" that extends into passage 23". Teeth 29" of the pawl face laterally to engage the ratchet teeth 21" of the strap when the parts are latched together (FIG. 12). FIG. 13 shows latching member 28" disengaged from strap 14" by the exertion of opposing forces parallel to plate 18" against first side wall 42 and second side wall 43. As shown, first side wall 42 tips laterally towards passage 23", web 50 flexes towards the relatively rigid side wall 43, and top wall 49 deforms primarily laterally and somewhat upwardly to cause latching member or pawl 28" to disengage from strap 14".

To limit the extent of lateral deformation of side wall 42 and to give a tactile signal to a user that a squeezing force sufficient to disengage the strap has been applied, the first side wall may be provided with stopping means. Such stopping means preferably takes the form of a stop member 52 that extends from first side wall 42 toward passage 23" such that when side wall 42 is urged toward side wall 43, stop member 52 is pivoted downwardly towards platform 45—preventing further inward flexure of side wall 42 when stop member 52 contacts platform 45. Stop member 52 can include an enlarged end portion 53 having a rounded bearing surface for engagement with platform 45.

Passage 23" in this embodiment is defined by a guide wall 30" having raised portion 54 and recess portions 55 that are adapted to receive the pair of longitudinal ribs 22" provided by strap 14". Preferably, platform 45 can also be provided with an upraised member 56 which in conjunction with raised and recessed portions 54 and 55, helps to maintain the position of strap 14" in passage 23".

The retention devices embodying this invention are believed particularly useful in the medical area, especially where such devices include adhesive pads for attachment to a patient's skin in the vicinity of the entry or exit site of a catheter or other tube. However, the retainer body with its elongated strap, and the releasable latching mechanism provided by the body which releases when a squeezing force is applied to opposite sides of the body, at least one of which is mounted for inward pivotal movement, may have other uses, some of which may be non-medical. Embodiments of the invention have therefore been disclosed in considerable detail for purposes of illustration, but it will be understood by those skilled in the art that many of these details may be varied without departing from the spirit and scope of the invention.

I claim:

1. A retention device for retaining objects, comprising a retainer body having a passage extending therethrough and having an elongated strap with one end portion joined at a junction to said body and an opposite free end portion insertable into and through said passage to form said strap into an object-retaining loop; said strap having a longitudinal series of transversely-extending ratchet teeth along one surface thereof; said body including a bottom platform; a first substantially flexible side wall pivotally connected to said platform, extending along said passage, and having an upper portion; a second substantially rigid side wall connected to said platform, extending along said passage and having an intermediate portion and an upper portion; a flexible top wall joined to said upper portion of said first side wall and being connected by a flexible web to said intermediate portion of said second side wall; and latching means extending downwardly from a central portion of said top wall for engaging said teeth and preventing reverse movement of said strap in said passage; said latching means being shifted out of engagement with said teeth when said first side wall is squeezed towards said second side wall to cause pivotal movement of said first side wall and lateral flexure of said central portion of said top wall.

2. The device of claim 1 in which said passage has an entrance located adjacent the junction of said body and said one end portion of said strap.

3. The device of claim 1 in which said body is mounted upon a flexible pad having upper and lower surfaces and having a pressure-sensitive adhesive layer along its lower surface.

4. The device of claim 1 in which said first side wall has a stopping means attached thereto for limiting lateral movement of said first side wall towards said second side wall.

5. A drainage tube retention device comprising a flexible pad having upper and lower surfaces and having a pressure-sensitive adhesive layer along its lower surface for adherence of the pad to a patient's skin; and tube retaining means mounted upon said upper surface comprising a retainer body having a passage extending therethrough; an elongated strap having one end portion joined at a junction to said body and an opposite free end portion insertable into and through said passage to form said strap into a loop for receiving and holding a draining tube; said strap having a longitudinal series of transversely-extending ratchet teeth along one surface thereof; said body having a bottom platform, a first substantially flexible side wall and a second substantially rigid side wall; said first and second side walls extending along said passage; said first side wall being pivotally connected to said platform; a flexible top wall joined to an upper portion of said first side wall at one end and having a flexible web at the other end joined to an intermediate portion of said second side wall; and latching means extending downwardly from a central portion of said top wall for engaging said teeth and preventing reverse movement of said strap in said passage; said latching means being moved laterally out of engagement with said teeth when said first side wall is pivoted towards said second side wall.

6. The device of claim 5 in which said passage has an entrance located adjacent the junction of said body and said one end of said strap.

7. The device of claim 5 in which said body also includes a guide wall for said passage that is substantially perpendicular to said pad.

8. The device of claim 7 in which said guide wall is imperforate.

9. The device of claim 8 in which said guide wall includes a laterally-facing channel-shaped recess means extending the length of said passage.

10. The device of claim 9 in which said strap includes longitudinal rib means along the surface thereof opposite from said one surface; said rib means being slideably receivable in said recess means.

11. The device of claim 7 in which said guide wall extends along a plane that substantially bisects said loop in an axial direction when said strap retains a drainage tube.

12. The device of claim 7 in which said latching means is provided with a lower end portion having a pawl that faces laterally towards said guide wall for engagement with said ratchet teeth when said strap extends into said passage and is supported by said guide wall.

13. The device of claim 5 in which said first side wall has a stopping means attached thereto for limiting lateral movement of said first side wall towards said second side wall.

* * * * *